United States Patent [19]

Perricone

[11] Patent Number: 5,879,690

[45] Date of Patent: *Mar. 9, 1999

[54] TOPICAL ADMINISTRATION OF CATECHOLAMINES AND RELATED COMPOUNDS TO SUBCUTANEOUS MUSCLE TISSUE USING PERCUTANEOUS PENETRATION ENHANCERS

[76] Inventor: Nicholas V. Perricone, 35 Pleasant St. Suite 2A, Meriden, Conn. 06450

[ * ] Notice: The term of this patent shall not extend beyond the expiration date of Pat. Nos. 5,554,647 and 5,643,586.

[21] Appl. No.: 851,222

[22] Filed: May 5, 1997

Related U.S. Application Data

[63] Continuation-in-part of Ser. No. 525,977, Sep. 7, 1995, Pat. No. 5,643,586.

[51] Int. Cl.[6] .................................................. A61K 7/48
[52] U.S. Cl. ..................... 424/401; 514/944; 424/DIG. 5
[58] Field of Search .............................. 424/401, DIG. 5; 514/944

[56] References Cited

U.S. PATENT DOCUMENTS

| | | |
|---|---|---|
| 4,590,067 | 5/1986 | Meisner . |
| 4,647,453 | 3/1987 | Meisner . |
| 4,772,591 | 9/1988 | Meisner . |
| 4,938,969 | 7/1990 | Schinitsky et al. ..................... 424/642 |
| 5,376,361 | 12/1994 | Perricone . |
| 5,554,647 | 9/1996 | Perricone ................. 514/474 |

OTHER PUBLICATIONS

Smith, E. W. and Maiback H. I.,"Percutaneous Penetration Enhancers", 1995, Book pp. 1–405.

*Primary Examiner*—Jyothsna Venkat
*Attorney, Agent, or Firm*—St. Onge Steward Johnston & Reens LLC

[57] ABSTRACT

Compositions for the topical treatment of sagging subcutaneous muscle and overlying cutaneous tissue contain an active ingredient exhibiting or producing catecholamine activity such as catecholamines and/or related compounds in a dermatologically acceptable carrier that contains at least one percutaneous penetration enhancer. Examplary catecholamines include adrenaline, norepinepherine, dopamine and their precursors; catecholamine precursors such as tyrosine and phenylalanine are preferred. Many embodiments, particularly those employing tyrosine and/or phenylalanine as a catecholamine precursor, further contain a neurotransmitter synthesis enhancer such as dimethylaminoethanol, and other co-factors such as vitamin $B_6$ and pantothenic acid or calcium pantothenate are included in the composition to enhance the action of the active ingredients. Other compounds that scavenge free radicals and antioxidants may also be added.

20 Claims, No Drawings

TOPICAL ADMINISTRATION OF CATECHOLAMINES AND RELATED COMPOUNDS TO SUBCUTANEOUS MUSCLE TISSUE USING PERCUTANEOUS PENETRATION ENHANCERS

RELATED APPLICATION DATA

This is a continuation-in-part of co-pending U.S. application Ser. No. 08/525,977, filed Sep. 7, 1995 now U.S. Pat. No. 5,643,586 (which is hereby incorporated herein in its entirety by reference).

TECHNICAL FIELD

This invention relates primarily to the treatment of subcutaneous muscles and overlying skin, particularly for faces that have developed prominent lines such as the nasolabial folds, hanging of tissue from the mandibular region, and increased sagging of tissue around the eyes observed in aging and other conditions such as myasthenia gravis, but also for the treatment of other bodily areas wherein sagging is observed, such as in the chest and breast region, and the upper arms and legs. The invention concerns compositions and methods of treating subcutaneous muscles and the overlying epidermis to ameliorate these changes, and improve the external appearance.

BACKGROUND OF THE INVENTION

With age, subcutaneous muscles lengthen and give a sagging appearance to the skin because underlying muscle is looser. Current treatments of flaccid skin and muscles from aging typically involve plastic surgery. The plastic surgeon cuts the skin and muscle and then pulls it taut, reducing some of the tissue and discarding it, then suturing it so that the facial, chest, arm, leg, and/or buttocks muscles remain tight.

The external appearance of aging individuals is particularly affected by subcutaneous changes in skeletal muscle tissue. When muscles are at rest, a certain amount of tautness usually remains. The residual degree of contraction in skeletal muscles is called muscle tone. In aging individuals, the degree of contraction relaxes, and is particularly obvious in the face.

In order for a muscle to contract, a message is sent from the brain to the spinal cord, and then from the spinal cord to the skeletal muscles. This is accomplished by an action potential which travels down the axon of the nerve. The nerve ends at an area called the synaptic knob, and this action potential causes the synaptic knob to release small diffusible chemical neurotransmitters into the synaptic cleft. The synaptic knob is rich in tiny vesicles containing neurotransmitters, and these vesicles are rich in acetylcholine in knobs innervating muscles. Acetylcholine is released into the synaptic cleft, and then meets the muscle at an invagination called the synaptic gutter. This acetylcholine then finds receptors on the muscle surface, which causes the muscle to become permeable to sodium ions, which result in membrane potential increases in the local area of the end plate, about 75 millivolts, creating a local potential called the end plate potential. This causes the muscle to contract.

Once this contraction takes place, the remaining acetylcholine in the cleft is destroyed by an enzyme called cholinesterase. The choline is reabsorbed by the presynaptic knob to be used again to synthesize acetylcholine. Thus, it is at this neuromuscular junction where acetylcholine causes its effect. The synaptic knobs have the capability of continually synthesizing new transmitter substance. This occurs mainly in the cytoplasm of the synaptic knobs, and then it is absorbed into tiny vesicles and stored as needed.

It can be seen that neurotransmission at neuromuscular junctions is a complicated process affected by many factors including the biosynthesis of the neurotransmitter, storage of the neurotransmitter, release of the neurotransmitter, interaction of the neurotransmitter with receptors on effector cells, and termination of neurotransmitter activity by reuptake and/or metabolic processes.

The process is further complicated by the interactions among neurotramnsmitters in the sympathetic and parasympathetic nervous systems. As described above, cholinergic neurons act at the myoneural junction and cause skeletal muscle contraction through the action of chemical mediators such as acetylcholine at synapses in the parasympathetic nervous system. In the sympathetic (autonomic) nervous system, adrenergic neurons employ other neurotransmitters at smooth muscle junctions, e.g., norepinephrine, epinephrine, dopamine, and serotonin. Norepinephrine is a mediator of activity at most post-ganglionic sympathetic endings in the autonomic nervous system. Neurotransmitters of the adrenergic neurons enhance neurotransmitters at the myoneural junction, e.g., acetylcholine release. Thus, epinephrine, an adrenergic catecholamine, can affect muscle contraction by enhancing the release and effects of acetylcholine at the myoneural junction.

The principal catecholamines found in the body, norephinephrine, epinephrine, and dopamine, are formed by hydroxylation and decarboxylation of the amino acids phenylalanine and tyrosine. Tyrosine is transported into adrenergic nerve endings by a concentrating mechanism. It is converted to dopa by hydroxylation and then decarboxylated to dopamine (3,4-dihydroxyphenylethylamine) in the cytoplasm of the neurons by tyrosine hydroxylase and dopa decarboxylase, respectively. The dopamine then enters the granulated vesicles from which it is converted to norepinephrine (noradrenaline) by dopamine β-hydroxylase. L-dopa is the isomer involved, and it is the L-isomer of norepinephrine that is produced. The rate-limiting step in synthesis is the conversion of tyrosine to dopa. Tyrosine hydroxylase which catalyzes this step is subject to feedback inhibition by dopamine and norepinephrine, thus providing internal control of the synthetic process. The co-factor for tyrosine hydroxylase is tetrahydrobiopterine, which is converted to dihydrobiopterine when tyrosine is converted to dopa.

Norepinepherine is synthesized in nerve endings but can also be resorbed by nerve endings after systemic secretion. This active uptake mechanism is characteristic of adrenergic neurons. It is also known that circulating norepinephrine and epinephrine (adrenaline, methylated norepinephrine) within the body are incorporated in small amounts by adrenergic neurons in the autonomic nervous system. Thus, adrenergic neurons differ from cholenergic neurons in the ability to uptake a complete molecule. Acetylcholine is not taken up to any appreciable degree, but the choline that is formed by the action of acetyl cholinesterase is taken up and recycled.

The aging process results in damage to presynaptic knobs, and therefore fewer neurotransmitters become available to a muscle for contraction. Receptor sites on muscle also deteriorate, and are unable to respond to the levels of acetylcholine present. Muscle tone maintained by nerve fibers releasing acetylcholine to small areas of muscle decreases, so that an appearance of sagging is observed.

In addition to changes in subcutaneous muscle tissue, the overlying epidermis thins and the skin appendages atrophy with age. Hair becomes sparse and sebaceous secretions decrease, with consequent susceptibility to dryness, chapping, and fissuring. The dermis diminishes with loss of elastic and collagen fibers. Typical treatment of sun-damaged and aged skin consists primarily of applications of various creams, lotions and gels to add moisture to the skin, as well as various acid peels to retexture the skin.

Cell age is due in part to free radical damage, which takes place mostly within the cell membrane. The cell membrane is most susceptible to attack by free radicals because of its dense molecular structure largely comprising lipids and lipoproteins, which are easily oxidized by reactive oxygen species. In the epidermis, reactive oxygen species, such as singlet oxygen, the superoxide anion, and hydroxyl radicals, and other free radicals are generated in normal metabolism, as well as through ultraviolet sun exposure, other forms of radiation, other environmental factors such as pollution or exposure to chemicals in the home or workplace, and the like. In addition, free radicals can activate chemical mediators of inflammation, particularly where arachadonic acid is released, which is then oxidized via two predominant pathways to produce either prostaglandins or leukotrines.

The body contains an endogenous antioxidant defense system made up of antioxidants such as vitamin E, vitamin C, superoxide dismutase, and glutathione. When metabolism increases or the body is subjected to other stress such as extreme exercise, radiation (ionizing and non-ionizing), or chemicals, the endogenous antioxidant systems are overwhelmed, and free radical damage takes place. Over the years, the cell membrane continually receives damage from reactive oxygen species and other free radicals, resulting in cross-linkage or cleavage of proteins and lipoproteins, and oxidation of membrane lipids and lipoproteins. Damage to the cell membrane can result in myriad changes including loss of cell permeability, increased intercellular ionic concentration, and decreased cellular capacity to excrete or detoxify waste products. As the intercellular ionic concentration of potassium increases, colloid density increases and m-RNA and protein synthesis are hampered, resulting in decreased cellular repair. Some cells become so dehydrated they cannot function at all.

In aging, the regularity of tissue structure is lost, and individual cells enlarge, but the total number of cells decreases approximately 30%. Intercellular collagen and elastin increases. The proportion of soluble collagen decreases, and there may be increased cross-linking between long-chain collagen macromolecules. Elastin loses its discrete structure and elasticity and has an increased calcium content.

Sunlight exposure wreaks far greater destruction on the skin than time itself, and intensifies and augments the aging process. Free radical damage to the surface of the skin from sun exposure is manifested as lines, mottling, discoloration, precancers and cancers. Aging of both skin and other tissues is, in part, the result of constant free radical damage to cell membranes, leading to decreased cell function. This results in accumulation of waste products in the cells, such as lipofuscin; increase in the potassium content of the cells, which results in dehydration of the cells; and decreased production of messenger RNA and proteins.

The combination of sagging subcutaneous muscles and aging skin contributes to the overall cosmetic changes typically observed in aging, such as wrinkling, which involves the transition of a formerly smooth skin surface to one that appears unevenly shrunk and/or contracted, and the effects of gravity on the aging skin overlying the muscle tissue. It would be desirable to reverse or diminish these effects without cosmetic surgery, and to treat other conditions exhibiting sagging muscles such as those observed in myasthenia gravis.

SUMMARY OF THE INVENTION

It is an object of this invention to provide a method for treating sagging subcutaneous muscle and overlying skin.

It is another and more specific object of the invention to provide a topical composition and method for shortening subcutaneous muscles, resulting in a lift in tissue on the face, chest, upper arms, upper legs or other area of application, while at the same time improving the overall condition of the overlying skin.

These and other objects are accomplished by the present invention, which provides a method for the topical treatment of subcutaneous muscle and overlying cutaneous tissue. The method comprises applying to the skin in affected areas a formulation containing an effective amount of at least one active ingredient exhibiting or producing catecholamine activity such as catecholamines, catecholamine precursors, catecholamine mimics, chemicals that augment the release of catecolamines, or mixtures thereof, and a percutaneous penetration enhancer in a dermatologically acceptable carrier. In many embodiments, the carrier and the enhancer are the same compound or mixtures of compounds. Active compounds are applied in amounts sufficient to increase subcutaneous muscle tone; typical concentrations of active ingredient range from about 0.1% to about 10% by weight. Catecholamines include epinephrine, norepinephrine, dopa, and serotonin; catecholamine precursors include tyrosine and phenylalanine; and catecholamine mimics include tyramine, ephedrine and amphetamine. Catecholamine precursors are particularly preferred.

Compositions of the invention further include at least one compound that enchances skin penetration so that active ingredients are delivered to the subcutaneous muscle layer. Percutaneous penetration enhancers include both chemical and physical enhancers, and mixtures thereof. Chemical penetration enhancers are preferred because these can be added to shelf-stable compositions containing the active ingredient or ingredients exhibiting or producing catecholamine activity in a dermatologically acceptable carrier that are easy for users to apply. Chemical penetration enhancers include, but are not limited to, sulfoxides, alcohols, polyols, alkanes, fatty acids, esters, amines and amides, terpenes, surface-active agents, cyclodextrins, and mixtures thereof, that are pharmacologically and chemically inert and chemically stable, potent, nonirritating, nonsensitizing, nonphototoxic, noncomedogenic, odorless, tasteless, colorless, and cosmetically acceptable. Preferred enhancers have a solubility parameter approximating that of the skin, i.e., 10.5 cal$^{1/2}$cm$^{3/2}$. These are typically present in compositions at a level of about 0.1% to 10%, more narrowly from about 0.5% to 5%, by weight.

Physical penetration enhancers include, but are not limited to, those enhancing skin hydration, occlusion devices, hydrocolloid patches and other transdermal delivery systems, lipophilic penetrants, delipidization, electroporation, iontophoresis, ultrasound, and the like methods known to skilled workers which increase skin permeability without toxicity and destruction of the stratum corneum.

Many embodiments additionally contain at least one additional compound that enhances neurotransmitter synthesis and/or provides other benefits to the dermatological composition such as radical scavengers and antioxidants. In some embodiments, for example, an acetylcholine precursor such as dimethylaminoethanol is included in the formulation with the catecholamine or related compound. In many embodiments, a single compound such as ascorbyl palmitate is employed as an ingredient to enhance several functional characteristics of inventive compositions, including skin penetration enhancement, free radical scavenging, and antioxidation.

Preferred embodiments also contain whatever cofactors augment the effect of the active ingredient. For example, in embodiments employing tyrosine, phenylalanine, or a mixture of these, pyridoxine (vitamin $B_6$) and calcium pantothenate or pantothenic acid (or mixtures of these) are typically employed. Antixodiants such as vitamin E acetate or sorbate, tocotrienol, ascorbic acid, or mixtures of any of these may be included in the formulation.

In one embodiment, the composition contains from about from about 1% to about 5% by weight, more narrowly from about 2% to about 3%, tyrosine or phenylalanine, or mixtures thereof and ingredients that facilitate the metabolic activity of these catecholamine precursors, namely, from about 0.25 to about 2 weight %, more narrowly from about 0.5% to about 1%, vitamin $B_6$, and from about 1 to about 10 weight %, more narrowly from about 2% to about 8%, vitamin C. This embodiment preferably further contains ascorbyl palmitate and at least one other ingredient that enhances neurotransmitter synthesis and/or skin penetration.

DETAILED DESCRIPTION OF THE INVENTION

This invention is based upon the surprising finding that subcutaneous muscle tissue can be treated by the topical application of an active ingredient that exhibits or produces catecholamine activity such as a catecholamine precursor to skin areas overlying the muscle where percutaneous penetration enhancement is employed. Substances that facilitate skin penetration as well as physical methods of transdermal delivery may be employed, but chemical enhancers are preferred for most embodiments because these can be easily incorporated into dermatological compositions that users can easily apply. Some preferred topical compositions also contain an acetylcholine precursor such as dimethylaminoethanol and/or other substances that enhance neurotransmitter synthesis, an antioxidant and other compounds that augment the efficacy of the topical composition, or prolong its shelf life.

In accordance with the present invention, at least one compound exhibiting or producing catecholamine activity such as a catecholamine or a catecholamine-related compound, in association with a dermatologically acceptable carrier in which the compound is dispersed or solubilized, is topically applied in effective amounts to skin areas which have been aged, or which are susceptible to age, in combination with a skin penetrant or delivery system so that active ingredient is provided to subcutaneous muscle layers. As will be discussed in greater detail below, in some embodiments, an acetylcholine precursor such as dimethylaminoethanol or other compound that enhances neurotransmitter synthesis is applied in admixture with the catecholamine or catecholamine-related compound.

By "catecholamine" is meant any one of a group of amines that act upon nerve cells as neurotransmitters or hormones. This group of similar compounds having a sympathomimetic action typically are molecules having an aromatic portion derived from catechol (2-hydroxyphenol) and an aliphatic amine portion. Catecholamines include, but are not limited to, dopamine (5-hydroxytryptamine), norepinephrine (noradrenaline; 4-(2-amino-1-hydroxyethyl)-1,2-benzenediol), and epinephrine (adrenaline; 4-(1-hydroxy-2-(methylamino)ethyl)-1,2-benzenediol). As used herein, dopa (3,4-dihydroxyphenylalanine) and serotonin (5-hydroxytryptamine) are also included in this group.

Catecholamine-related compounds include catecholamine precursors, catecholamine mimics, chemicals that augment the release of catecholamines, and mixtures of these with each other and with catecholamine. Catecholamine precursors include any in the synthetic pathway such as, for example, tyrosine, phenylalanine, and mixtures thereof. Catecholamine mimics include, but are not limited to, sympathomimetic amines that function similarly, augmenting, for example, the release of norepinepherine, such as tyramine, ephedrine, amphetamine, and mixtures thereof. Chemicals that augment the release of catecholamines specifically include those that augment release such as co-factors of enzymes in the metabolic pathway, e.g., tetrahydrobiopterin and pyridoxine, as well as inhibitors of enzymes that inactivate catecholamines such as inhibitors of catechol-O-methyltransferase and monoamine oxidase.

Compositions useful in methods of the invention include at least one percutaneous penetration enhancer that augments delivery of active ingredient to subcutaneous muscle layers. Percutaneous penetration enhancers include both chemical and physical enhancers, and mixtures thereof.

Any chemical penetration enhancer known to skilled workers can be used in the practice of the invention. Preferred enhancers are pharmacologically and chemically inert and chemically stable, potent, nonirritating, nonsensitizing, nonphototoxic, noncomedogenic, odorless, tasteless, colorless, and cosmetically acceptable. Chemical enhancers include, but are not limited to, sulfoxides such as dimethylsulfoxide and decylmethylsulfoxide; alcohols such as ethanol, propanol, butanol, pentanol, hexanol, octanol, nonanol, decanol, lauryl alcohol, myristyl alcohol, cetyl alcohol, stearyl alcohol, oleyl alcohol, linoleyl alcohol, linolenyl alcohol and benzyl alcohol; polyols such as propylene glycol, polyethylene glycol, ethylene glycol, diethylene glycol, triethylene glycol, dipropylene glycol, glycerol, propanediol, butanediol, pentanediol, hexanetriol; alkanes; fatty acids such as valeric, heptanoic, pelargonic, caproic, capric, lauric, myristic, stearic, oleic, and caprylic acids; esters such as methyl acetate, ethyl acetate, butyl acetate, methyl valerate, methyl propionate, diethyl sebacate, ethyl oleate, isopropyl butyrate, isopropyl hexanoate, isopropyl decanoate, isopropyl myristate, isopropyl palmitate; amines and amides such as urea, dimethylacetamide, diethyltoluamide, dimethylformamide, dimethyloctamide, dimethyldecamide, biodegradable cyclic urea (1-alkyl-4-imidazolin-2-one), pyrrolidone derivatives (1-methyl-2-pyrrolidone, 2-pyrrolidone, 1-lauryl-2-pyrrolidone, 1-methyl-4-carboxy-2-pyrrolidone, 1-hexyl-4-carboxy-2-pyrrolidone, 1-lauryl-4-carboxy-2-pyrrolidone, 1-methyl-4-methoxycarbonyl-2-pyrrolidone, 1-hexyl- and 1-lauryl- 4-methoxycarbonyl-2-pyrrolidone, N-cyclohexylpyrrolidone, N-dimethylaminopropylpyrrolidone, N-cocoalkylpyrrolidone, N-tallowalkylpyrrolidone, as well as biodegradable pyrrolidone derivatives such as fatty acid esters of N-(2-hydroxyethyl)-2-pyrrolidone), cyclic amides (e.g., 1-dodecylazacycloheptane-2-one (Azone®), 1-geranylazacycloheptan-2-one, 1-farnesylazacycloheptan-2-one, 1-geranylgeranylazacycloheptan-2-one, 1-(3,7-dimethyloctyl)azacycloheptan-2-one, 1-(3,7,11- trimethyldodecyl)azacycloheptan-2-one, 1-geranylazacyclohexane-2-one, 1-geranylazacyclopentan-2,5-dione, and 1-farensylazacyclopentan-2-one), hexamethylenelauramide and its derivatives; diethanolamine, triethanolamine; terpenes, including hydrocarbon (e.g.:, D-limonene, α-pinene, and β-carene), alcohol (α-terpinol, terpinen-4-ol, and carvol), ketones (e.g., Carvone™, pulegone, piperitone, and menthone), oxide (e.g., cyclohexene oxide, limonene oxide, α-pinene oxide, cyclopentene oxide, and 1,8-cineole), and oil derivatives (e.g., Ylang ylang, anise chenopodium, and eucalyptus); surfactants, including anionic (e.g., sodium laurate and/or sodium lauryl sulfate), cationic (e.g., cetyltrimethyl ammonium bromide, tetradecyltrimethylammonium bromide, benzalkonium chloride, octadecyltrimethylammonium chloride, cetylpyridinium chloride, dodecyltrimethylammonium chloride, and hexadecyltrimethylammonium chloride), nonionics (Poloxamer™, Brij™, Span™, Tween™, Myrj™, and Miglol™ products), bile salts (e.g., sodium chlolate and/or the sodium salts of taurocholic, glycolic, and desoxycholic acids), and lecithin; cyclodextrins; alkanones (e.g., N-heptane, N-octane, N-decane, N-undecane, N-dodecane, N-tridecane, N-tetradecane, and N-hexadecane); organic acids (e.g., salicylic acid and salicylates, including their methyl, ethyl, and propyl glycol derivatives, citric acid, and succinic acid); and mixtures thereof, such those discussed in Smith, E. W., and Maibach, H. I., eds., *Percutaneous Penetration Enhancers*, CRC Press, New York, 1995, pages 1 to 28, 45 to 136, 211 to 220, 245 to 258, 335 to 342 and the references cited therein). Compositions may also contain acrylate/ceteth copolymers or compounds that interrupt the stratum corneum barrier disclosed in Smith and Maibach, cited above. Preferred enhancers have a solubility parameter approximating that of the skin, i.e., 10.5 cal$^{1/2}$cm$^{3/2}$.

Penetration enhancers are added in amounts effective to deliver active ingredient to subcutaneous muscle layers when compositions of the invention are applied topically to overlying skin. Enhancers are typically present in compositions of the invention at a level of about 0.1% to 10%, more narrowly from about 0.5% to 5%, by weight. Urea, oleic acid, and/or fatty acid esters of ascorbic acid are employed as enhancers in some embodiments. Example formulations are given hereafter.

Physical penetration enhancers may also be employed, alone, or in combination with chemical percutaneous enhancers. Physical enhancers include, but are not limited to, those enhancing skin hydration, occlusion devices, hydrocolloid patches and other transdermal delivery systems, lipophilic penetrants including liposomes, delipidization, electroporation, ultrasound, iontophoresis, and the like methods known to skilled workers which increase skin permeability without toxicity and destruction of the stratum corneum as described on pages 21 to 28, 35 to 44, 323 to 334, and 351 to 406 of Smith and Maibach, cited above.

In many preferred embodiments, the active ingredient is a catecholamine precursor such as tyrosine or phenylalanine or mixtures thereof. In these embodiments, cofactors such vitamin $B_6$ and pantothenate or pantothenic acid are typically employed to achieve a maximal metabolic effect. In some embodiments, an acetylcholine precursor is added to the composition; dimethylaminoethanol is used in one embodiment. As is more fully discussed below, vitamin C may and/or a fatty acid ester of ascorbic acid such as ascorbyl palmitate are also added in some embodiments.

Many preferred compositions further contain at least one additional substance that directly or indirectly enhances catecholamine activity and/or neurotransmitter synthesis such as pyridoxine, calcium pantothenate, zinc, and mixtures of any of these, and another antioxidant such as vitamin E acetate or sorbate, tocotrienol, ascorbic acid, or mixtures of any of these. By the term "acetylcholine precursor" is meant any precursor in the biosynthetic pathway of acetylcholine, or related pathways. These include co-factors and precursors of acetylcholine, synthetic enzymes and precursors or enhancers of acetylCoA production. Acetylcholine precursors include, but are not limited to, dimethylaminoethanol, monoaminoethanol, choline, serine, and mixtures thereof. As used herein, "precursors" also include derivatives of precursors such as esters, e.g., acetic acid and parachlorophenylacetic acid esters of dimethylaminoethanol or monoaminothanol, and the like. Folic acid and vitamin $B_{12}$ augment acetylcholine synthesis in some embodiments. Other embodiments contain choline acetylase agonists and acetylcholinesterase inhibitors to augment acetylcholine synthesis. Dimethylaminoethanol is a preferred precursor. An advantage of embodiments of the invention containing dimethylaminoethanol is that the compound also acts as a penetration enhancer to deliver active ingredient to subcutaneous layers after application of the composition.

At least one compound exhibiting or producing catecholamine activity such as catecholamines and/or catecholamine-related compounds are typically used in topical compositions ascorbic acid (vitamin C) and/or an ascorbic acid derivative or precursor. As used herein, the term "ascorbic acid" includes the free acid, its salts, e.g., calcium ascorbate, magnesium ascorbate, potassium ascorbate, sodium ascorbate, magnesium ascorbyl phosphate, other derivatives, and mixtures thereof. Derivatives include, but are not limited to, salts, ascorbic acid anhydride and ascorbic acid esters, or mixtures of any of these. Fatty acid esters are preferred because these not only act as antioxidant, but also (as described above) typically penetrate the skin more efficaciously than other derivatives, as well as acting as an antioxidant and free radical scavenger. As used herein, the term "fatty acid esters of ascorbic acid" include any saturated or unsaturated fatty acid ester of ascorbic acid and mixtures of these esters. Because of their lack of susceptibility to oxidation and the development of off-odors in stored compositions, saturated fatty acid esters of ascorbic acid are especially preferred. These include, but are not limited to, ascorbyl palmitate, ascorbyl laurate, ascorbyl myristate, ascorbyl stearate, and mixtures thereof.

Ascorbyl palmitate is employed in one embodiment. "Ascorbyl palmitate" includes the pure compound and esters enriched with ascorbyl palmitate such as those obtained by acylating ascorbic acid with fatty acids from feedstock oils or feedstock oil fractions containing primarily palmitic acid. The term includes preparations and liposomes containing the compound.

The amount of compound exhibiting or producing catecholamine activity such as a catecholamine and/or catecholamine-related compound necessary to bring about the therapeutic treatment of subcutaneous muscle and overlying skin is not fixed per se, and necessarily is dependent upon the severity and extent of the aged tissue, the efficacy of the carrier in skin penetration, the particular catecholamine or related compound employed and additional antioxidants and agents enhancing neurotransmitter synthesis such as acetylcholine precursors employed, and the concentrations of these ingredients in the formulation put together in association with a dermatologically acceptable carrier that penetrates the skin. Preferred embodiments employ active ingredients in amounts effective to achieve a clinically perceptable increase in subcutaneous muscle tone by topical application of the composition. As discussed above, agents that enhance skin penetration are employed in amounts effective to deliver active ingredients to subcutaneous muscle tissue.

Typical embodiments contain from about 0.1% to 10% by weight, more narrowly from about 0.25% to about 7%, even more narrowly, from about 3% to 5%, catecholamine or related compound. Lower amounts of active compound are included in some formulations having especially efficacious percutaneous penetrants; for example, some embodiments thus contain from about 0.25% to about 3% active compound. Other embodiments contain higher amounts, e.g., from about 1% to about 7% active compound. Many embodiments contain from about 3% to 5% active compound.

Compositions of the invention are typically applied in admixture with a dermatologically acceptable carrier or vehicle (e.g., as a lotion, cream, ointment, soap, or the like), but, as mentioned above, the percutaneous penetration enhancer or mixture of enhancers may also serve as carrier. Topical application is facilitated and, in some cases, additional therapeutic effects are provided as might be brought about, e.g., by moisturizing of the affected skin areas and by enhancing penetration of active ingredients. When a carrier is employed, it is necessary that the carrier be inert in the sense of not bringing about a deactivation of active ingredients, and in the sense of not bringing about any adverse effect on the skin to which it is applied. Many preferred carriers function well as penetration enhancers or augment the effect of other ingredients so that active compound is efficiently delivered to subcutaneous muscle tissue.

Suitable carriers include water, alcohols, oils and the like, chosen for their ability to dissolve or disperse the active ingredients at concentrations of active ingredients most suitable for use in the therapeutic treatment. Generally, even low concentrations of active ingredients in a carrier will be suitable, requiring only that more frequent topical application be resorted to. As a practical matter, however, to avoid the need for repeated application, it is desirable that the topically applied composition (e.g., catecholamine and/or related compounds in association with other ingredients in a carrier) be formulated to contain at least about 0.25% by weight, more preferably at least about 1% by weight, and most preferably at least about 2% by weight, of the catecholamine or related compound. In one embodiment, the composition contains from about from about 1 to about 5 weight %, more narrowly from about 2% to about 3%, tyrosine or phenylalanine, or mixtures thereof; from about 0.25 to about 2 weight %, more narrowly from about 0.5% to about 1%, vitamin $B_6$, and from about 1 to about 10 weight %, more narrowly from about 2% to about 8%, vitamin C. Carriers are chosen which solubilize or disperse the active ingredients at such concentrations, and in some cases to penetrate the skin to deliver them to subcutaneous muscle tissue.

Preferred compositions of the invention contain at least one additional substance that enhances neurotransmitter synthesis such as an acetylcholine precursor, pyridoxine, folic acid, vitamin $B_{12}$, calcium pantothenate, pantothenic acid, zinc, and mixtures of any of these, and another antioxidant such as vitamin E, vitamin E acetate, vitamin E sorbate, vitamin E succinate, tocotrienol, ascorbic acid, or mixtures of any of these. Preferred compositions are formulated to retain at least about 90% activity for at least about 6 months, preferably a year, when stored at room temperature (i.e., 20°to 25° C.). The formulation can also contain additional ingredients such as membrane stabilizers.

In some embodiments, the compositions contain tocotrienols or derivatives thereof for enhanced therapeutic or prophylactic treatment as described in U.S. Pat. No. 5,376, 361 to Perricone (which is hereby incorporated herein in its entirety by reference). These are particularly advantageous because tocotrienols are oily so that they physically contributes to the lubrication and soothing of affected skin areas as well as penetration. Reductive agents such as $\alpha$-hydroxy acids can, optionally, be utilized with the tocotrienols for a means for yet further enhancing the efficacy of the compositions. Glycolic acid is preferred in one embodiment.

As used herein, the term "tocotrienol" encompasses tocopherols bearing unsaturated tails, including, but not limited to, naturally occurring $\alpha$-, $\beta$-, $\gamma$-, and $\delta$- tocotrienols, desmethyl-tocotrienol, didesmethyl-tocotrienol, their synthetic counterparts, their counterparts having methylated or demethylated chroman rings, stabilized derivatives such as those having the phenolic hydroxyl functionality acylated with an organic acid to form an ester such as acetates and succinates, and mixtures thereof. The term also includes tocotrienol-enriched fractions and tocotrienol-enriched vitamin E preparations.

Where tocotrienols are employed, the amount of tocotrienol or one or more derivatives thereof (hereinafter referred to collectively as tocotrienol for ease of reference) necessary to bring about enhanced prevention and/or therapeutic skin treatment in conjunction with catecholamines and/or catecholamine-related compounds (and optionally other ingredients described above) is not fixed per se, and necessarily is dependent upon the identity and form of tocotrienol employed, the concentration of tocotrienol when employed as a tocotrienol-enriched vitamin E preparation and/or with a carrier, the amount and type of other ingredients, the user's skin type, and, where present, the severity and extent of the patient's pathological skin condition. Many embodiments contain from about 0.025% to 0.25% tocotrienol.

While the carrier for the catecholamines and/or related compounds, and optionally, other ingredients (such as acetylcholine precursors and/or fatty acid esters of ascorbic acid) can consist of a relatively simple solvent or dispersant such as water or oils, it is generally preferred that the carrier be one which aids in percutaneous delivery and penetration of the active ingredients into lipid layers and subcutaneous muscle tissue as discussed above. Moreover, the composition preferably is one that is conducive to topical application, and particularly one that can be applied so as to localize the application. Many such compositions are known in the art, and can take the form of lotions, creams, gels or even solid compositions (e.g., stick-form preparations). Typical compositions include lotions containing water and/ or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers. Most preferred carriers for use with active ingredients of the invention are fat-soluble, i.e., those which can effectively penetrate skin layers and deliver the active ingredients to the lipid-rich layers of the skin and to subcutaneous muscle tissue.

Generally, the composition is topically applied to the affected skin areas in a predetermined or as-needed regimen to bring about improvement, it generally being the case that gradual improvement is noted with each successive application. Insofar as has been determined based upon clinical studies to date, no adverse side effects are encountered.

When tyrosine is applied to skin in a dermatologically acceptable carrier, there is clinically visible increased muscle tone and the overlying skin feels like silk after application. In an assessment of the efficacy of a composition of the invention, an aqueous suspension made up of approximately 7% by weight ascorbyl palmitate, 3% dimethylaminoethanol, 2% by weight vitamin E acetate, 1/2% by weight of vitamin $B_6$ (pyridoxine), 1% by weight zinc sulfate (weighed as zinc), 1% by weight calcium pantothenate, and 2% by weight tyrosine is applied to facial skin. Within 3 to 5 minutes of application, the facial skin becomes more taut. A reduction of nasolabial folds is observed, as well as a general tightening of the face in the periorbital region and the forehead. This effect lasts for approximately 24 hours, and, when the formulation is reapplied on a daily basis, after about a month, there appears to be a marked shortening of muscle tissue resulting in a more youthful appearance. The formulation can also be placed on the pectoralis area and in the area of breast tissue, resulting in an uplifted look to that area. Applications of inventive formulations can also benefit the appearance of arms and legs, particularly upper arms and thighs. Formulations can also be applied to the faces of myasthenia gravis patients to improve their appearance.

While not wishing to be bound to any theory, by providing catecholamine-related compounds, muscle tone is increased and the resultant shortening of muscles lifts tissue on the face, chest, or other areas where the composition is applied. It is believed that the presence of catecholamines or catecholamine-related compounds, particularly catecholamine precursors, as well as other compounds involved in catecholamine production and neurotransmitter synthesis, such as vitamin C, vitamin $B_6$ (pyridoxine), calcium pantothenate or pantothenic acid, and zinc, appears to help boost levels of acetylcholine in the neuromuscular junction, resulting in increased muscle tone, particularly where nerve synapses interact with involuntary muscles. This increased muscle tone causes a slight shortening of the muscle, and over a period of time, the muscle actually does become shorter. A shorter muscle results in a lifting of overlying skin, with the cosmetic appearance of a diminishment of sagging. Catecholamines have also been implicated in glycogenolygic effects that are particularly evident in muscle tissue.

As disclosed in U.S. Pat. Nos. 4,647,453 and 4,772,591 to Meisner, a combination of precursors of norepinephrine, ascorbic acid, and an anti-inflammatory have been suggested to have efficacy in the treatment for tissue degenerative inflammatory disease and wound healing. The treatment was not formulated for skin penetration, however. Schinitsky and Meisner further suggested a diminution of fine wrinkling when a combination of tyrosine and water-soluble zinc salt were applied to the skin, but the composition also did not-penetrate the skin and caused irritation in some subjects (U.S. Pat. No. 4,938,969).

In addition, where additional preferred ingredients discussed above are employed, treatment in accordance with the present invention helps prevent free radical damage to skin and helps reverse cell membrane damage by application of free radical scavengers and quenchers. It is important to have free radical scavengers in the cell membrane that protect the target site and have a greater affinity for free radicals than the target tissue. As a free radical scavenger or neutralizer, ascorbyl palmitate, because of its palmitic fatty acid side chain, intersperses in membranes more effectively, and therefore provides better protection for cell membranes during free radical attack. Substances that stabilize membranes or increase endogenous glutathione production further prevent free radical damage to the cell and membrane structures. In membranes, vitamin E also provides protection from free radical damage.

Moreover, fatty acid esters of ascorbic acid such as ascorbyl palmitate aid or accelerate collagen synthesis, so as to remedy the depeleted collagen observed in aging. By virtue of its fat solubility, fatty acid esters of ascorbic acid enhance percutaneous delivery of catecholamine precursors and related compounds as well as acetylcholine precursors such as dimethylaminoethanol if they are part of the formulation.

Again, while not wishing to be bound to any theory, the special efficacy of methods of the invention may in part be due to the multiple functions catecholamines play in the system. In addition to the fact that the compounds facilitate acetylcholine release, they serve also as penetration enhancers, which help absorption of other active ingredients in embodiments where these are included in the compositions applied to the skin. Catecholamines and related compounds also act as antioxidants. In the practice of the invention, they exert this activity interspersed within lipid-rich membranes, areas that other topical compositions typically do not reach.

The application of free radical scavengers and topical antiinflammatories with substances that cause a shortening of muscles, produces increased tone, provides a composition that enhances the appearance of the skin, and results in a smoother, tighter, and more youthful appearance for aging-persons and patients afflicted with conditions that cause sagging faces such as myasthenia gravis.

Acetylcholine receptors are found on human epidermal keratinocytes. When these are occupied, they can affect keratinocyte growth, resulting in a more youthful appearance, enhancing the effects of compositions of the invention because they increase acetylcholine production.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all modifications and variations be included within the scope of the invention. The claims are meant to cover the claimed components and steps in any arrangement or sequence which is effective to meet the objectives intended for the invention, unless the context specifically indicates the contrary.

I claim:

1. A method for the treatment of subcutaneous muscle tissue comprising topically applying to affected skin areas overlying the muscle tissue a composition comprising, as an active ingredient, from about 0.1% to about 10% by weight of a compound exhibiting catecholamine activity selected from the group consisting of dopamine, norepinephrine, epinephrine, dopa, serotonin, tyrosine, phenalanine, tyramine, ephedrine, amphetamine, tetrahydrobiopterin, pyridoxine, and mixtures thereof, and an effective amount of a percutaneous penetration enhancer, so that muscle tone in the subcutaneous muscle tissue is increased.

2. A method according to claim 1 wherein the composition comprises from about 0.25% to about 5% by weight active ingredient.

3. A method according to claim 1 wherein the percutaneous penetration enhancer is a chemical enhancer.

4. A method according to claim 3 wherein the enhancer is selected from the group consisting of sulfoxides, alcohols, polyols, alkanes, fatty acids, esters, amines, amides, terpenes, surface-active agents, cyclodextrins, and mixtures thereof.

5. A method according to claim 4 wherein the enhancer has a solubility parameter of about 10.5 $cal^{1/2}cm^{3/2}$.

6. A method according to claim 3 wherein the enhancer is selected from the group consisting of oleic acid, urea, a saturated fatty acid ester of ascorbic acid, a tocotrienol, and mixtures thereof.

7. A method according to claim 6 wherein the fatty acid ester of ascorbic acid is primarily ascorbyl palmitate.

8. A method according to claim 1 wherein the percutaneous penetration enhancer is a physical enhancer.

9. A method according to claim 8 wherein the physical enhancer is selected from the group consisting of a skin hydration enhancer, an occlusion device, a hydrocolloid patch, a lipophilic penetrant, a delipidization agent, electroporation, iontophoresis, and ultrasound.

10. A method according to claim 1 wherein the enhancer comprises a chemical enhancer and a physical enhancer.

11. A method according to claim 1 wherein the active ingredient is tyrosine.

12. A method according to claim 11 wherein the composition contains from about 1% to about 3% by weight tyrosine.

13. A method according to claim 1 wherein the composition further contains another ingredient that enhances neurotransmitter synthesis.

14. A method according to claim 13 wherein the composition further comprises a compound selected from the group consisting of pyridoxine, calcium pantothenate, pantothenic acid, and mixtures thereof.

15. A method according to claim 1 wherein the composition further comprises an antioxidant.

16. A method for the topical treatment of aging subcutaneous muscle tissue comprising topically applying to affected skin areas overlying the tissue, in a dermatologically acceptable carrier, a composition comprising from about 0.25% to about 5% by weight of an active ingredient selected from the group consisting of dopa, tyrosine, phenylalanine, and mixtures thereof, to clinically perceptibly increase muscle tone in the subcutaneous muscle tissue, wherein the composition further comprises from about 0.1% to about 10% by weight of a penetration enhancer selected from the group consisting of sulfoxides, alcohols, polyols, alkanes, fatty acids, esters, amines and amides, terpenes, surface-active agents, cyclodextrins, and mixtures thereof.

17. A method according to claim 16 wherein the penetraton enhancer is selected from the group consisting of a saturated fatty acid ester of ascorbic acid, oleic acid, urea, tocotrienol, and mixtures thereof.

18. A method for the treatment of aging subcutaneous muscle tissue comprising administering to the overlying epidermis of said muscle tissue a composition comprising tyrosine and a chemical penetration enhancer selected from the group consisting of sulfoxides, alcohols, polyols, alkanes, fatty acids, esters, amines and amides, tepenes, surface-active agents, cyclodextrins, and mixtures thereof in amounts effective to deliver tyrosine to the muscle tissue.

19. A method according to claim 18 wherein the composition contains from about 0.25% to about 5% by weight tyrosine.

20. A method according to claim 18 wherein the composition comprises ascorbyl palmitate.

* * * * *